(12) United States Patent
Urick

(10) Patent No.: US 6,352,501 B1
(45) Date of Patent: Mar. 5, 2002

(54) ADJUSTABLE RADIATION SOURCE

(75) Inventor: Michael J. Urick, Rogers, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/404,388

(22) Filed: Sep. 23, 1999

(51) Int. Cl.[7] .......................... A61M 29/02; A61N 5/00

(52) U.S. Cl. ............................................. 600/3

(58) Field of Search ....................... 600/1–8

(56) References Cited

U.S. PATENT DOCUMENTS

| | | |
|---|---|---|
| 2,546,761 A | 3/1951 | Loftus |
| 2,862,108 A | 11/1958 | Meilink |
| 2,955,208 A | 10/1960 | Stevens |
| 3,060,924 A | 10/1962 | Rush |
| 3,147,383 A | 9/1964 | Prest |
| 3,324,847 A | 6/1967 | Zoumbolis |
| 3,505,991 A | 4/1970 | Hellerstein et al. |
| 3,643,096 A | 2/1972 | Jeffries, Jr. et al. |
| 3,669,093 A | 6/1972 | Sauerwein et al. |
| 3,674,006 A | 7/1972 | Holmer |
| 3,750,653 A | 8/1973 | Simon |
| 3,811,426 A | 5/1974 | Culver et al. |
| 3,861,380 A | 1/1975 | Chassagne et al. |
| 3,866,050 A | 2/1975 | Whitfield |
| 3,927,325 A | 12/1975 | Hungate et al. |
| 4,096,862 A | 6/1978 | DeLuca |
| 4,220,864 A | 9/1980 | Sauerwein et al. |
| 4,225,790 A | 9/1980 | Parson, Jr. et al. |
| 4,233,517 A * | 11/1980 | Van't Hooft .................... 600/3 |
| 4,244,357 A | 1/1981 | Morrison |
| 4,281,252 A | 7/1981 | Parsons, Jr. et al. |
| 4,314,157 A | 2/1982 | Gaines |
| 4,364,376 A | 12/1982 | Bigham |

(List continued on next page.)

FOREIGN PATENT DOCUMENTS

| | | |
|---|---|---|
| CA | 2166915 A | 8/1996 |
| DE | 91 02 312.2 | 8/1992 |
| DE | 195 26 680 A1 | 1/1997 |

(List continued on next page.)

OTHER PUBLICATIONS

Tjho–Heslinga et al., "Results of ruthenium irradiation of uveal melanona", *Radiothereapy Oncology*, vol. 29, pp 33–38, Dec. 1993.

Lommatzsch et al., "Radiation effects on the optic nerve observed after brachytherapy of choroidal melanomas with 106Ru/106Rh plaques", *Graefe's Arch. Clin. Exp. Opthalmology* vol. 232, pp. 482–487, Dec. 1994.

*Radiotherapy of Intraoculare and Orbital Tumors*, Springer–Verlak publishers, Berlin Heidelberg and New York, copyright Dec. 1993, pp. 23–30 and 363–367.

Fackelmann, "Harbinger of a Heart Attack", *Science News*, vol. 151, Jun. 14, 1997, pp. 374–375.

Raloff, "Nuclear Medicine Gets Friendlier—Experimental Therapies Seek to Poison Just the Disease", *Science News*, vol. 152, Jul. 19, 1997, pp. 40–41.

Sutherland, "Managing Cancer Through Synergy", *Administrative Radiology Journal*, Nov. 1996, pp. 21–27.

*Primary Examiner*—Samuel G. Gilbert
(74) *Attorney, Agent, or Firm*—Crompton, Seager & Tufte, LLC

(57) ABSTRACT

An intravascular medical device including an elongate shaft and a variable-length ionizing radiation source disposed on the distal end thereof. The present invention may be manifested as a source wire, a guide wire, a catheter or other suitable intravascular device with an adjustable length radiation source. For example, the adjustable source may be implemented on a wire having a variable-length radioactive tip, on a balloon catheter having a variable-length balloon inflated with a radioactive fluid, or on a catheter having means for advancing and retracting radioactive seeds of variable number and/or spacing.

12 Claims, 12 Drawing Sheets

U.S. PATENT DOCUMENTS

| | | | |
|---|---|---|---|
| 4,584,991 A | 4/1986 | Tokita et al. | |
| 4,588,395 A | 5/1986 | Lemelson | |
| 4,631,415 A | 12/1986 | Sauerwein et al. | |
| 4,702,228 A | 10/1987 | Russell, Jr. et al. | |
| 4,706,652 A | 11/1987 | Horowitz | |
| 4,763,642 A | 8/1988 | Horowitz | |
| 4,763,671 A | 8/1988 | Goffinet | |
| 4,782,834 A | 11/1988 | Maguire et al. | |
| 4,784,116 A | 11/1988 | Russell, Jr. et al. | |
| 4,815,449 A | 3/1989 | Horowitz | |
| 4,819,618 A | 4/1989 | Liprie | |
| 4,851,694 A | 7/1989 | Rague et al. | |
| 4,861,520 A | 8/1989 | van't Hooft et al. | |
| 4,881,937 A | 11/1989 | van't Hooft et al. | |
| 4,897,076 A | 1/1990 | Puthawala et al. | |
| 4,936,823 A | 6/1990 | Colvin et al. | |
| 4,963,128 A | 10/1990 | Daniel et al. | |
| 4,969,863 A | 11/1990 | van't Hooft et al. | |
| 4,976,266 A | 12/1990 | Huffman et al. | |
| 4,976,680 A | 12/1990 | Hayman et al. | |
| 4,976,690 A | 12/1990 | Solar et al. | |
| 5,030,194 A | 7/1991 | Van't Hooft | |
| 5,032,113 A | 7/1991 | Burns | |
| 5,059,166 A | 10/1991 | Fischell et al. | |
| 5,084,001 A | 1/1992 | Van't Hooft et al. | |
| 5,084,002 A | 1/1992 | Liprie | |
| 5,092,834 A | 3/1992 | Ishiwara et al. | |
| 5,120,973 A | 6/1992 | Rohe et al. | |
| 5,139,473 A | 8/1992 | Bradshaw et al. | |
| 5,141,487 A | 8/1992 | Liprie | |
| 5,147,282 A | 9/1992 | Kan | |
| 5,163,896 A | 11/1992 | Suthanthiran et al. | |
| 5,176,617 A | 1/1993 | Fischell et al. | |
| 5,183,455 A | 2/1993 | Hayman et al. | |
| 5,199,939 A | 4/1993 | Dake et al. | |
| 5,213,561 A * | 5/1993 | Weinstein et al. | 600/7 |
| 5,261,879 A | 11/1993 | Brill | |
| 5,267,960 A | 12/1993 | Hayman et al. | |
| 5,282,781 A | 2/1994 | Liprie | |
| 5,302,168 A | 4/1994 | Hess | |
| 5,344,383 A | 9/1994 | Liping | |
| 5,354,257 A * | 10/1994 | Roubin et al. | 600/7 |
| 5,370,685 A | 12/1994 | Stevens | |
| 5,391,139 A | 2/1995 | Edmundson | |
| 5,395,300 A | 3/1995 | Liprie | |
| 5,405,309 A | 4/1995 | Carden, Jr. | |
| 5,409,015 A | 4/1995 | Palermo | |
| 5,411,466 A | 5/1995 | Hess | |
| 5,425,720 A | 6/1995 | Rogalsky et al. | |
| 5,429,582 A | 7/1995 | Williams | |
| 5,484,384 A | 1/1996 | Fearnot | |
| 5,498,227 A | 3/1996 | Mawad | |
| 5,503,613 A | 4/1996 | Weinberger | |
| 5,503,614 A | 4/1996 | Liprie | |
| 5,532,122 A | 7/1996 | Drukier | |
| 5,538,494 A | 7/1996 | Matsuda | |
| 5,540,659 A | 7/1996 | Teirstein | |
| 5,556,389 A | 9/1996 | Liprie | |
| 5,575,749 A | 11/1996 | Liprie | |
| 5,575,771 A | 11/1996 | Walinsky | |
| 5,605,530 A | 2/1997 | Fischell et al. | |
| 5,611,767 A | 3/1997 | Williams | |
| 5,616,114 A | 4/1997 | Thornton et al. | |
| 5,618,266 A | 4/1997 | Liprie | |
| 5,624,372 A | 4/1997 | Liprie | |
| 5,643,171 A | 7/1997 | Bradshaw et al. | |
| 5,649,924 A | 7/1997 | Everett et al. | |
| 5,653,683 A | 8/1997 | D'Andrea | |
| 5,662,580 A | 9/1997 | Bradshaw et al. | |
| 5,674,177 A | 10/1997 | Hehrlein et al. | |
| 5,683,345 A * | 11/1997 | Waksman et al. | 600/3 |
| 5,688,220 A | 11/1997 | Verin et al. | |
| 5,707,332 A | 1/1998 | Weinberger | |
| 5,713,828 A | 2/1998 | Coniglione | |
| 5,720,717 A | 2/1998 | D'Andrea | |
| 5,722,984 A | 3/1998 | Fischell et al. | |
| 5,728,042 A | 3/1998 | Schwager | |
| 5,730,698 A | 3/1998 | Fischell et al. | |
| 5,776,099 A | 7/1998 | Tremulis | |
| 5,782,740 A | 7/1998 | Schneiderman | |
| 5,782,742 A | 7/1998 | Crocker et al. | |
| 5,795,286 A | 8/1998 | Fischell et al. | |
| 5,800,333 A | 9/1998 | Liprie | |
| 5,803,895 A | 9/1998 | Kronholz et al. | |
| 5,807,231 A | 9/1998 | Liprie | |
| 5,816,259 A | 10/1998 | Rose | |
| 5,816,999 A | 10/1998 | Bischoff et al. | |
| 5,820,553 A | 10/1998 | Hughes | |
| 5,833,593 A | 11/1998 | Liprie | |
| 5,840,008 A | 11/1998 | Klein et al. | |
| 5,840,009 A | 11/1998 | Fischell et al. | |
| 5,840,064 A | 11/1998 | Liprie | |
| 5,843,163 A | 12/1998 | Wall | |
| 5,851,171 A | 12/1998 | Gasson | |
| 5,851,172 A | 12/1998 | Bueche et al. | |
| 5,855,546 A | 1/1999 | Coletti | |
| 5,857,956 A | 1/1999 | Liprie | |
| 5,863,284 A | 1/1999 | Klein | |
| 5,863,285 A | 2/1999 | Hastings et al. | |
| 5,865,720 A | 2/1999 | Hastings et al. | |
| 5,871,436 A | 2/1999 | Eury | |
| 5,871,437 A | 2/1999 | Alt | |
| 5,873,811 A | 2/1999 | Wang et al. | |
| 5,879,282 A | 3/1999 | Fischell et al. | |
| 5,882,290 A | 3/1999 | Kume | |
| 5,882,291 A | 3/1999 | Bradshaw et al. | |
| 5,891,091 A | 4/1999 | Teirstein | |
| 5,897,573 A | 4/1999 | Rosenthal et al. | |
| 5,899,882 A | 5/1999 | Waksman et al. | |
| 5,906,573 A | 5/1999 | Aretz | |
| 5,910,101 A | 6/1999 | Andrews et al. | |
| 5,910,102 A | 6/1999 | Hastings | |
| 5,913,813 A | 6/1999 | Williams et al. | |
| 5,916,143 A | 6/1999 | Apple et al. | |
| 5,919,126 A | 7/1999 | Armini | |
| 5,924,973 A | 7/1999 | Weinberger | |
| 5,924,974 A | 7/1999 | Loffler | |
| 5,938,582 A | 8/1999 | Ciamacco, Jr. et al. | |
| 5,947,899 A | 9/1999 | Hehrlein | |
| 5,947,924 A | 9/1999 | Liprie | |
| 5,947,958 A | 9/1999 | Woodard et al. | |
| 5,957,829 A | 9/1999 | Thornton | |
| 5,961,439 A | 10/1999 | Chernomorsky et al. | |
| 5,967,966 A | 10/1999 | Kornholz et al. | |
| 5,971,909 A | 10/1999 | Bradshaw et al. | |
| 5,976,106 A | 11/1999 | Verin et al. | |
| 5,997,462 A | 12/1999 | Loffler | |
| 5,997,463 A | 12/1999 | Cutter | |
| 6,010,445 A | 1/2000 | Armini et al. | |
| 6,013,019 A | 1/2000 | Fischell et al. | |
| 6,013,020 A * | 1/2000 | Meloul et al. | 600/7 |
| 6,024,690 A | 2/2000 | Lee et al. | |
| 6,030,333 A | 2/2000 | Sioshansi et al. | |
| 6,033,357 A | 3/2000 | Ciezki et al. | |
| 6,149,574 A * | 11/2000 | Trauthen et al. | 600/3 |

FOREIGN PATENT DOCUMENTS

| | | |
|---|---|---|
| DE | 197 54 870 A1 | 8/1998 |
| DE | 197 24 233 C1 | 12/1998 |
| DE | 197 58 234 | 7/1999 |
| DE | 198 07 727 | 7/1999 |

| | | |
|---|---|---|
| DE | 198 25 563 | 12/1999 |
| DE | 198 25 999 | 12/1999 |
| DE | 198 26 000 | 12/1999 |
| DE | 198 29 447 | 1/2000 |
| EP | 0 360 582 | 8/1990 |
| EP | 0 514 913 A2 | 11/1992 |
| EP | 0 633 041 A1 | 1/1995 |
| EP | 0 686 342 A1 | 12/1995 |
| EP | 0 688 580 A1 | 12/1995 |
| EP | 0 696 906 B1 | 2/1996 |
| EP | 0 749 764 A1 | 12/1996 |
| EP | 0 754 472 A2 | 1/1997 |
| EP | 0 754 473 A2 | 1/1997 |
| EP | 0 593 136 B1 | 3/1997 |
| EP | 0 788 051 A1 | 6/1997 |
| EP | 0 801 961 A2 | 10/1997 |
| EP | 0 810 004 | 12/1997 |
| EP | 0 813 894 A2 | 12/1997 |
| EP | 0 629 380 B1 | 7/1998 |
| EP | 0 865 803 | 9/1998 |
| EP | 0 904 798 | 3/1999 |
| JP | 10071210 | 3/1998 |
| WO | WO 86/03124 | 6/1986 |
| WO | WO 93/04735 | 3/1993 |
| WO | WO 94/25106 | 11/1994 |
| WO | WO 94/26205 | 11/1994 |
| WO | WO 95/07732 | 3/1995 |
| WO | WO 96/06654 | 3/1996 |
| WO | WO 96/10436 | 4/1996 |
| WO | WO 96/13303 | 5/1996 |
| WO | WO 96/14898 | 5/1996 |
| WO | WO 96/17654 | 6/1996 |
| WO | WO 96/22121 | 7/1996 |
| WO | WO 96/29943 | 10/1996 |
| WO | WO 96/40352 | 12/1996 |
| WO | WO 97/07740 | 3/1997 |
| WO | WO 97/09937 | 3/1997 |
| WO | WO 97/17029 | 5/1997 |
| WO | WO 97/18012 | 5/1997 |
| WO | WO 97/19706 | 6/1997 |
| WO | WO 97/25102 | 7/1997 |
| WO | WO 97/25103 | 7/1997 |
| WO | WO 97/40889 | 11/1997 |
| WO | WO 98/01183 | 1/1998 |
| WO | WO 98/01184 | 1/1998 |
| WO | WO 98/01185 | 1/1998 |
| WO | WO 98/01186 | 1/1998 |
| WO | WO 98/11936 | 3/1998 |
| WO | WO 98/16151 | 4/1998 |
| WO | WO 98/20935 | 5/1998 |
| WO | WO 98/25674 | 6/1998 |
| WO | WO 98/24049 | 7/1998 |
| WO | WO 98/30273 | 7/1998 |
| WO | WO 98/34681 | 8/1998 |
| WO | WO 98/36788 | 8/1998 |
| WO | WO 98/36790 | 8/1998 |
| WO | WO 98/36796 | 8/1998 |
| WO | WO 98/39052 | 9/1998 |
| WO | WO 98/39062 | 9/1998 |
| WO | WO 98/39063 | 9/1998 |
| WO | WO 98/40032 | 9/1998 |
| WO | WO 98/46309 | 10/1998 |
| WO | WO 98/55179 | 12/1998 |
| WO | WO 98/57706 | 12/1998 |
| WO | WO 99/01179 | 1/1999 |
| WO | WO 99/02219 | 1/1999 |
| WO | WO 99/04706 | 2/1999 |
| WO | WO 99/04856 | 2/1999 |
| WO | WO 99/10045 | 3/1999 |
| WO | WO 99/21615 | 5/1999 |
| WO | WO 99/21616 | 5/1999 |
| WO | WO 99/22774 | 5/1999 |
| WO | WO 99/22775 | 5/1999 |
| WO | WO 99/22812 | 5/1999 |
| WO | WO 99/22815 | 5/1999 |
| WO | WO 99/24116 | 5/1999 |
| WO | WO 99/24117 | 5/1999 |
| WO | WO 99/29354 | 6/1999 |
| WO | WO 99/29370 | 6/1999 |
| WO | WO 99/29371 | 6/1999 |
| WO | WO 99/30779 | 6/1999 |
| WO | WO 99/34969 | 7/1999 |
| WO | WO 99/36121 | 7/1999 |
| WO | WO 99/39628 | 8/1999 |
| WO | WO 99/40962 | 8/1999 |
| WO | WO 99/40970 | 8/1999 |
| WO | WO 99/40971 | 8/1999 |
| WO | WO 99/40972 | 8/1999 |
| WO | WO 99/40973 | 8/1999 |
| WO | WO 99/40974 | 8/1999 |
| WO | WO 99/42162 | 8/1999 |
| WO | WO 99/42163 | 8/1999 |
| WO | WO 99/42177 | 8/1999 |
| WO | WO 99/44686 | 9/1999 |
| WO | WO 99/44687 | 9/1999 |
| WO | WO 99/49935 | 10/1999 |
| WO | WO 99/56825 | 11/1999 |
| WO | WO 99/56828 | 11/1999 |
| WO | WO 99/61107 | 12/1999 |
| WO | WO 99/62598 | 12/1999 |
| WO | WO 99/66979 | 12/1999 |
| WO | WO 00/03292 | 1/2000 |
| WO | WO 00/04838 | 2/2000 |
| WO | WO 00/04953 | 2/2000 |
| WO | WO 00/09212 | 2/2000 |

\* cited by examiner

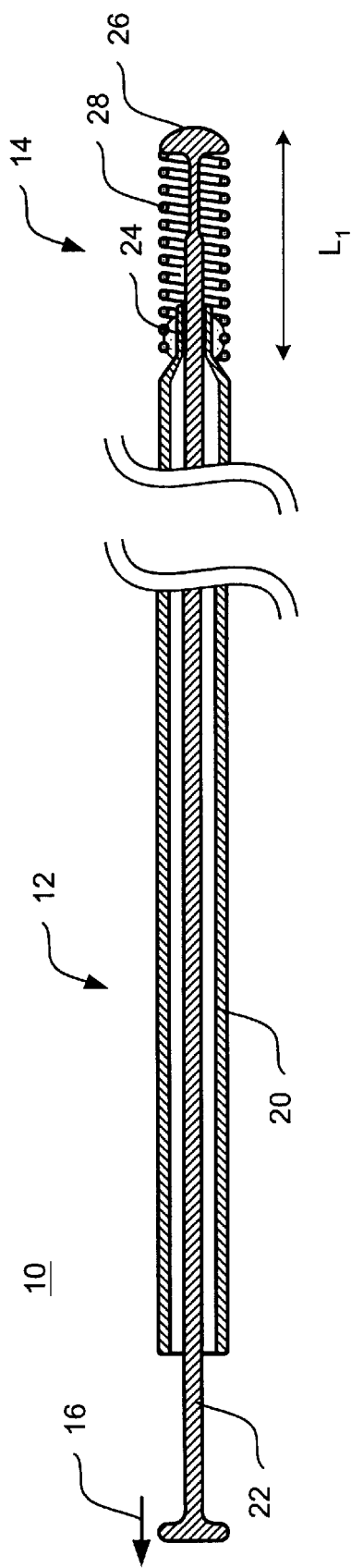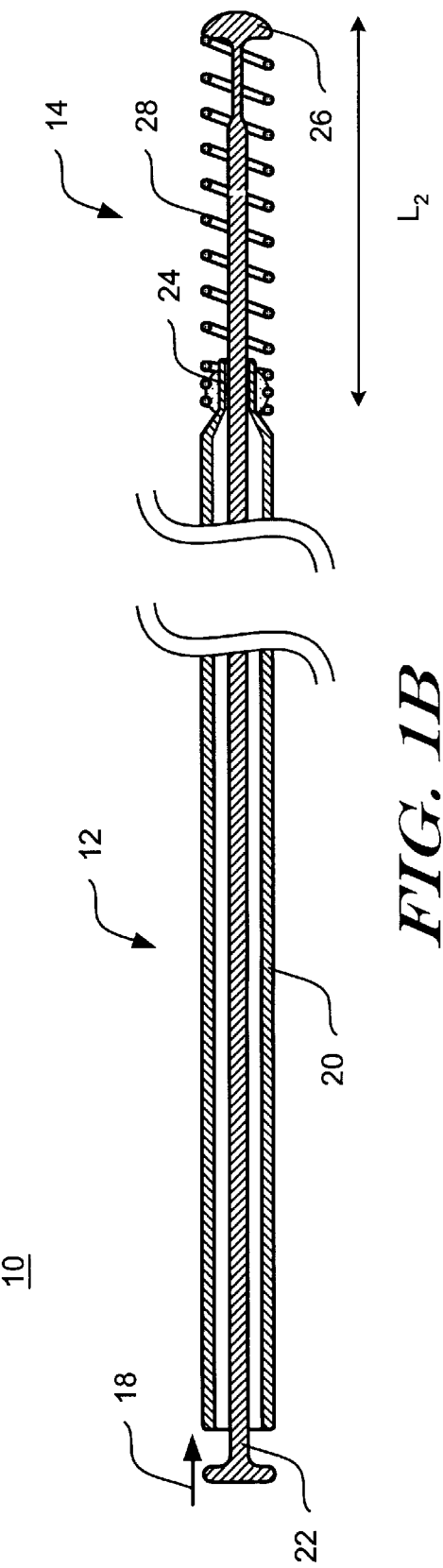

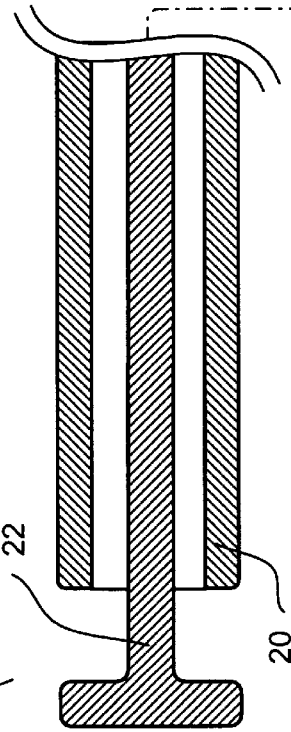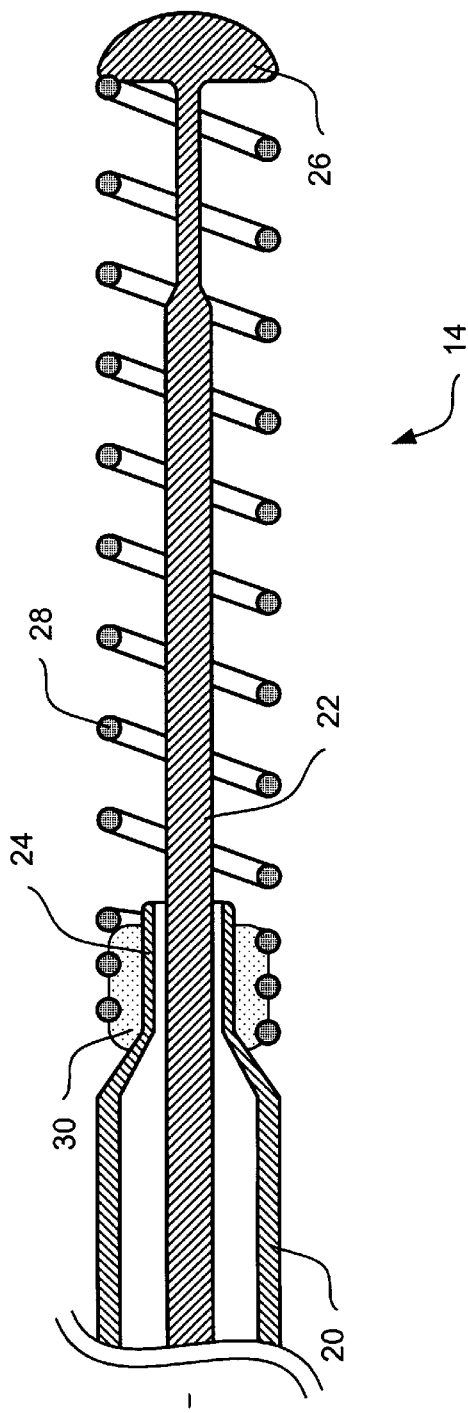
FIG. 2B

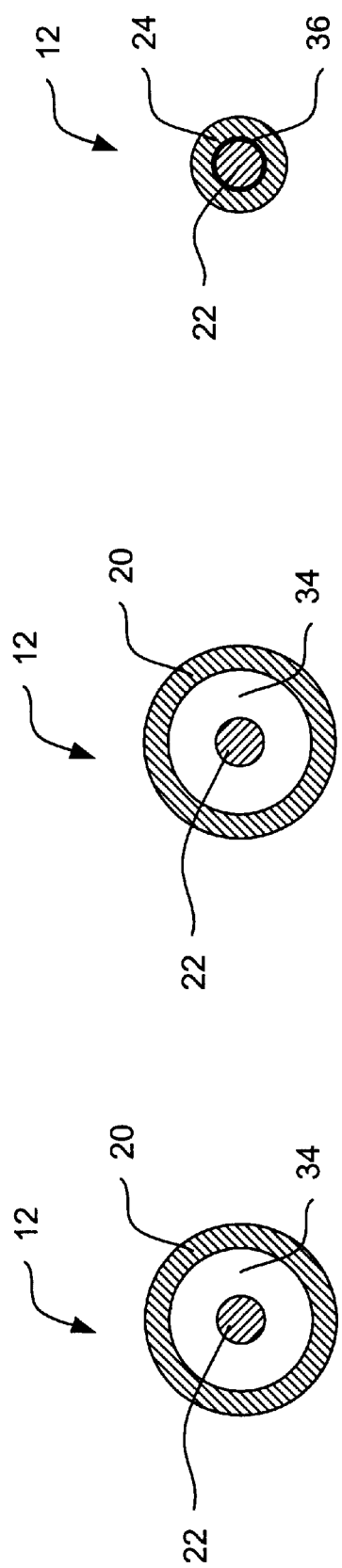

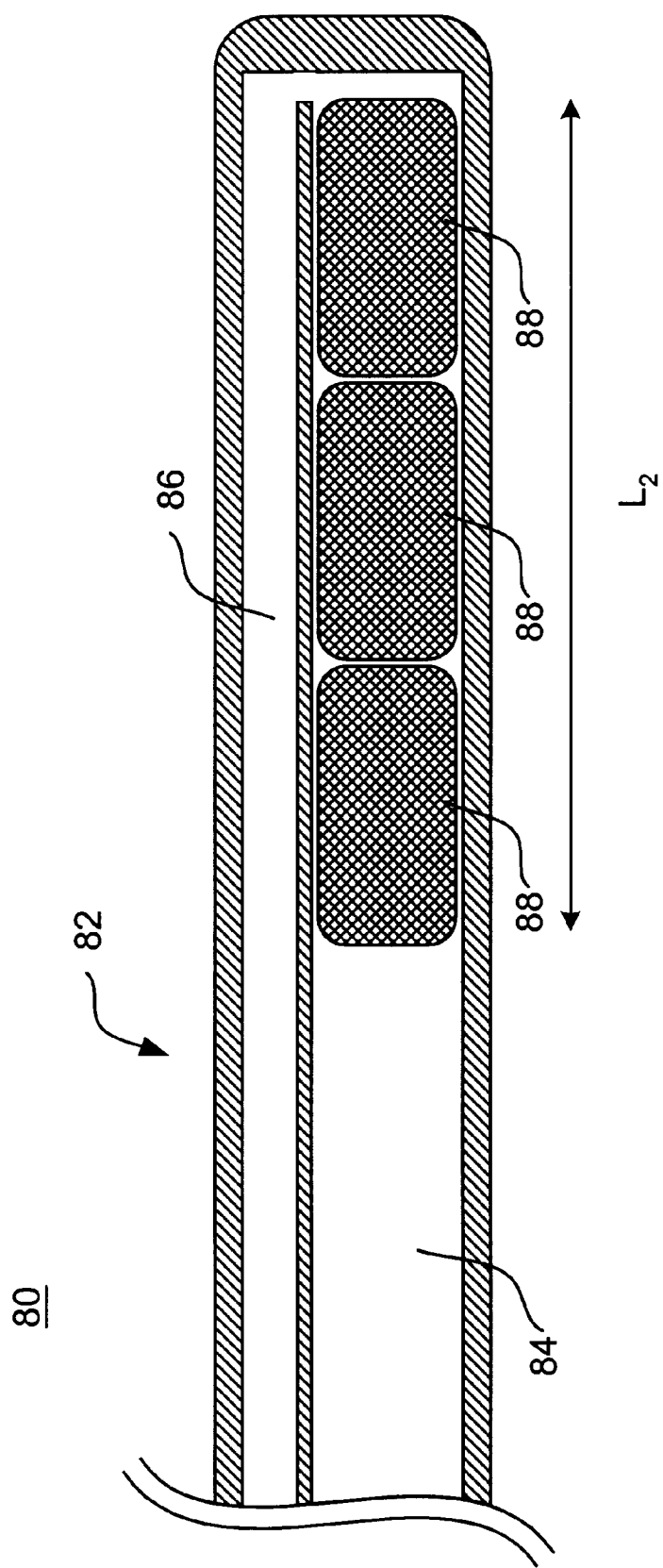

ADJUSTABLE RADIATION SOURCE

FIELD OF THE INVENTION

The present invention generally relates to medical devices. More specifically, the present invention relates to medical devices suitable for intravascular ionizing radiation therapy.

BACKGROUND OF THE INVENTION

Intravascular ionizing radiation therapy is being used increasingly to treat vascular disease. For example, intravascular ionizing radiation therapy has been proposed as both a primary and a secondary therapy for treating vascular restrictions. Clinical studies have shown that ionizing radiation may be used to inhibit or prevent restenosis after percutaneous transluminal angioplasty (PTA). In coronary applications, such vascular restrictions may range in length from a few millimeters to several centimeters, depending on the extent and nature of the disease, in addition to the size and type of vessel affected.

Typically, physicians evaluate the size (length and diameter) and nature of the vascular restriction in order to determine the appropriate treatment length and the corresponding ionizing radiation device to be used for treatment. However, intravascular ionizing radiation devices commonly utilize a fixed-length radiation source, and the number of different sizes available is limited. Accordingly, in some instances, the physician is not be able to select the correct radiation source length. Such limitations may leave the physician with no alternative but to select an intravascular ionizing radiation device having an improper radiation source length.

Thus, when utilizing an ionizing radiation device having a fixed-length radiation source disposed on the distal end thereof, clinical circumstances often give rise to a mismatch between the length of the radiation source and the length of the treatment site. Specifically, the length of the radiation source may be too long or too short as compared to the length of the treatment site. If the radiation source is too long, healthy tissue disposed at either end of the treatment site will inevitably be exposed to ionizing radiation. Exposing healthy tissue to ionizing radiation is clearly an undesirable event.

If the radiation source is too short, it is necessary to reposition the fixed-length radiation source in the vessel. Unless the treatment site is an exact whole number multiple of the length of the radiation source and the radiation source is precisely repositioned, various areas of the treatment site will inevitably have more or less radiation exposure than other areas of the treatment site. Repositioning the radiation source may result in overlapping exposure or healthy tissue exposure. Even if the treatment site length is an exact whole number multiple of the length of the radiation source, repositioning of a relatively short radiation source may be inherently imprecise and may require an increase in dwell time, both of which are not desirable. As a result, it is common for various regions of the treatment site to be either underexposed or overexposed to ionizing radiation due to a mismatch in length between the treatment site and the radiation source.

An example of a clinical implication of selecting an ionizing radiation device having an improper radiation source length has been observed, and is commonly referred to as the "candy wrapper" effect. The "candy wrapper" effect occurs when the length of the radiation source does not entirely cover the desired treatment site, thus, potentially leaving opposite ends of the vascular restriction untreated. The untreated regions of the vascular restriction may tend to restenos or re-occlude over time. The "candy wrapper" effect may be compounded when a beta radiation source is used, due to the shorter depth penetration of beta radiation. As such, the conventional practice is to expose the treatment site to ionizing radiation beyond the proximal and distal ends of the restriction to avoid the "candy wrapper" effect. However, such practice may expose otherwise healthy vascular tissue to potentially harmful ionizing radiation.

To address the issue of mismatched treatment length and radiation source length, ionizing radiation devices that utilize a moveable shield have been proposed. For example, U.S. Pat. No. 5,213,561 to Weinstein et al. discloses a device for preventing restenosis after angioplasty, wherein the device includes a radioactive source and a moveable shield in the form of an longitudinally shiftable sleeve to selectively expose the radioactive source. Shielded devices such as this allow adjustments to be made during the procedure in order to change the length of the exposure. Unfortunately, however, such fixed-length shielded devices tend to be stiff and relatively large, making it difficult to position the shielded portion of the device in tortuous or small diameter vasculature.

SUMMARY OF THE INVENTION

The present invention overcomes these disadvantages by providing an intravascular medical device including an elongate shaft and a variable-length ionizing radiation source disposed on the distal end thereof. The present invention may comprise a source wire, a guide wire, a catheter or other suitable intravascular device with an adjustable length radiation source. In one embodiment, the adjustable source is implemented on a wire having a variable-length radioactive tip. In another embodiment, the adjustable source is implemented on a balloon catheter having a variable-length balloon inflated with a radioactive fluid. In yet another embodiment, the adjustable source is implemented on a catheter having means for advancing and retracting radioactive seeds of variable number and/or spacing.

The intravascular device of the present invention provides a variable-length radiation source to compensate for any mismatch in length that would otherwise occur between a fixed-length radiation source and the treatment site. Thus, the variable-length design of the present invention improves the match between the radiation source length and the treatment site length. In addition, the variable-length design of the present invention reduces the inventory that must be kept on hand to treat different patients with different treatment site lengths, thereby reducing the otherwise significant cost of storing radioactive material. As compared to fixed-length devices of the prior art that require a shield to vary radiation exposure, the variable-length design of the present invention provides a more flexible and lower profile device by eliminating the need for a shield.

As implemented on a wire having a variable-length radioactive tip, the tip may comprise a coil, a braid, an elastomeric tube, or other suitable structure capable of longitudinal expansion and contraction. The radiation source may be formed of radioactive material, or the radiation source may be formed of an inert base material with a radioactive coating, dispersion, impregnation, composite, etc., thereon or therein. To affect variations in length of the source, the elongate shaft may include an outer tube and a movable core wire disposed therein. In this embodiment, the proximal end of the radiation source is connected to the distal end of the outer tube, and the distal end of the radiation source is connected to the distal end of the core wire. With this arrangement, longitudinal displacement of the core wire relative to the outer tube causes corresponding longitudinal displacement of the distal end of the radiation source, which in turn causes longitudinal expansion or contraction of the radiation source. Thus, both the length of the ionizing radiation source and the radioactivity per unit length may be varied.

As implemented on a balloon catheter having a variable-length balloon inflated with a radioactive fluid, the length of the balloon may be varied by a number of different means. For example, the length of the balloon may be varied by selectively retracting a constraining sleeve disposed about the balloon. Alternatively, the length of the balloon may be varied by utilizing an inverting balloon and selectively extending one end of the balloon. Any desired radioactive fluid and/or suspension may be used in conjunction with the variable-length balloon.

As implemented on a catheter having means for advancing and retracting radioactive seeds, either the number, spacing or both may be varied to effectively control the length of the radiation source. The seeds or pellets may be advanced and retracted by pneumatic means or by mechanical means.

BRIEF DESCRIPTION OF THE DRAWINGS

FIGS. 1A and 1B are longitudinal cross-sectional views of the present invention in the form of an elongate wire having a variable-length radioactive tip. FIG. 1A shows the variable-length tip in the contracted (i.e., short) state, and FIG. 1B shows the variable-length tip in the extended (i.e., long) state;

FIGS. 2A and 2B are detailed longitudinal cross-sectional views of the elongate wire shown in FIGS. 1A and 1B, respectively;

FIGS. 3, 4 and 5 are lateral cross sectional views taken along lines 3—3, 4—4 and 5—5, respectively, in FIG. 2A;

FIG. 6A shows the variable-length balloon in the unrestrained position, and FIG. 6B shows the variable-length balloon in the restrained position;

FIG. 7A shows the variable-length balloon in the extended position, and FIG. 7B shows the variable-length balloon in the contracted position;

FIGS. 8A and 8B are longitudinal cross-sectional views of the present invention in the form of a catheter having means for advancing and retracting radioactive seeds of variable number. FIG. 8A shows the catheter having several seeds disposed in the distal end thereof to define a long radioactive section, and FIG. 8B shows fewer seeds to define a short radioactive section; FIG. 9A shows the catheter having several spacers between the seeds to define a long radioactive section, and FIG. 9B shows fewer spacers between the seeds to define a short radioactive section.

DETAILED DESCRIPTION OF THE INVENTION

Figure 2A:
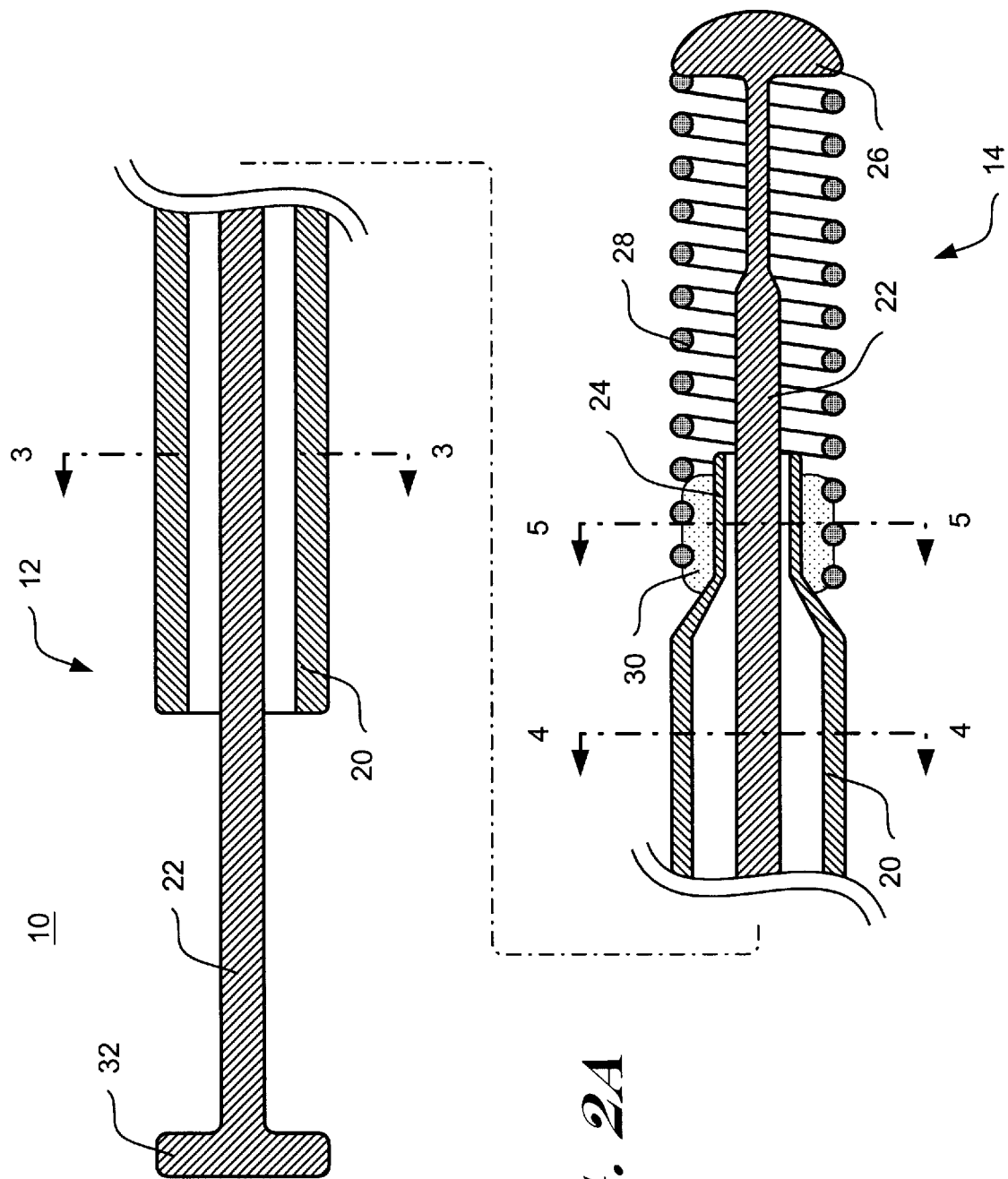

The following detailed description should be read with reference to the drawings in which similar elements in different drawings are numbered the same. The drawings, which are not necessarily to scale, depict illustrative embodiments and are not intended to limit the scope of the invention.

Refer to FIGS. 1A and 1B, which illustrate longitudinal cross-sectional views of the medical device of the present invention in the form of an elongate wire 10. Although illustrated as a wire 10, the medical device of the present invention may be manifested in a wide variety of forms. For example, the medical device of the present invention may take the form of a guide wire, a source wire, a centering device, a simple tubular catheter, a balloon catheter, or other suitable intravascular device. For purposes of illustration only, the present invention has been described with reference to a wire 10 having an extendable radioactive tip (FIGS. 1A–5), catheters 40/60 having a variable-length balloon filled with radioactive fluid (FIGS. 6A–7B), and a catheter 80 having means for advancing and retracting radioactive seeds of variable number and/or spacing (FIGS. 8A–9B).

Regardless of the specific embodiment, the medical device of the present invention includes an elongate shaft suitable for intravascular navigation and a variable-length ionizing radiation source disposed on the distal end thereof. In addition, regardless of the specific embodiment, the medical device of the present invention includes a means to vary the length of the radiation source. For example, in the elongate wire 10 embodiment illustrated in FIGS. 1A and 1B, the wire 10 a variable-length ionizing radiation source or extendable tip 14 disposed on the distal end of a shaft 12. Also in this embodiment, the means for varying the length of the tip 14 comprises an outer tubular member 20 having a moveable core 22 disposed therein.

The means by which the length of the extendable tip 14 is varied may comprise a moveable core 22 disposed in an outer tubular member 20 as illustrated, but may also comprise a wide variety of other suitable mechanisms. The primary objective of a suitable mechanism is to cause longitudinal displacement of the distal end of the tip 14 relative to the proximal end of the tip 14. Such longitudinal displacement thereby causes corresponding longitudinal contraction or expansion of the tip 14. With this objective in mind, those skilled in the art will readily appreciate that other suitable mechanisms may be employed.

For example, two elongate members disposed side-by-side may be connected to opposite ends of the extendable tip 14, wherein the elongate members may be longitudinally displaced relative to each other to affect changes in length of the tip 14. Alternatively, similar to the embodiment illustrated, two tubular elongate members co-longitudinally disposed may be connected to opposite ends of the tip 14. Skilled artisans will recognize that these and many other mechanical linkages may be employed to affect changes in length of the tip 14.

As an alternative to mechanical linkages, longitudinal contraction or expansion of the tip 14 may be accomplished by pneumatic mechanisms. For example, a proximal end of the tip 14 may be connected to a hollow cylinder, with the distal end of the tip 14 connected to a piston disposed in the hollow cylinder. Fluid pressure may be delivered to the hollow cylinder by a variety of means in order to pneumatically control longitudinal displacement of the piston disposed therein. With this arrangement, longitudinal contraction or expansion of the tip 14 may be affected by changing the pressure delivered to the hollow cylinder. Those skilled in the art will recognize that these examples are merely illustrative, as a wide variety of means, including mechanical and pneumatic means, may be employed without departing from the scope or spirit of the invention.

Referring to the particular embodiment illustrated in FIGS. 1A and 1B, the proximal end of the extendable tip 14 is connected to the distal end 24 of the outer tubular member 20. The distal end of the tip 14 is connected to the distal end of the core member 22. With this arrangement, longitudinal displacement of the distal end 26 of the core member 22 relative to the distal end 24 of the outer tubular member 20 causes corresponding longitudinal displacement of the distal end of the tip 14. Longitudinal contraction or expansion, in turn, is caused by longitudinal displacement of the distal end of the tip 14.

Specifically, moveable core member 22 may be retracted in the proximal direction relative to shaft 12 as indicated by arrow 16 to cause the variable-length tip 14 to longitudinally contract to a length L1 as illustrated in FIG. 1B. In addition, core member 22 may be advanced in the distal direction relative to shaft 12 as indicated by arrow 18 to cause longitudinal expansion of the variable-length tip 14 to a second length L2 as illustrated in FIG. 1B. With this arrangement, the length of the tip 14 may be varied from an longitudinally contracted length L1 to an longitudinally expanded length L2, where L2 is greater than L1, by actuating the core member 22 relative to the outer tubular member 20 as indicated by arrows 16 and 18. The core member 22 may be manually actuated relative to the outer tubular member 20 by the treating physician. Alternatively, a pneumatic or mechanical actuator may be used to displace the core member 22 relative to the outer tubular member 20. Such an actuator may be disposed in the afterloader.

The extendable tip 14 may comprise a coil 28 as shown or may comprise a variety of other structures capable of longitudinal contraction and expansion. For example, the tip 14 may comprise a braid or an elastomeric tube. For purposes of illustration only, the tip 14 has been shown in the form of a coil. Tip 14 may be formed of a radioactive material or may be formed of an inert base material having a radioactive material disposed thereon or therein. For example, a base material of stainless steel may be utilized with a radioactive material comprising P32 plated thereon. If the tip 14 is in the form of an elastomeric tube, the radioactive material may comprise small particles dispersed in the wall of the polymer tube. Suitable base materials for a coil or braid structure include stainless steel, gold, and platinum. Preferably, the base material comprises a radiopaque material to facilitate radiographic visualization and navigation with the assistance of fluoroscopy. In the case of an elastomeric tube, suitable base materials include silicone, polyurethane, or other biocompatible elastomeric polymers. Suitable radioactive materials include W188, Sr90, Ru106, Y90, Ir192 and P32. The particular form of the tip 14 and the particular base and radioactive materials of the tip 14 are not particularly critical as long as the tip 14 is variable-length and functional in the vasculature.

The variable-length tip 14 preferably has a uniform radioactivity, aside from natural decay. With a constant radioactivity, variations in length of the tip 14 cause corresponding variations in radioactivity per unit length. As compared to a conventional shielded fixed-length radiation source, the total radiation dose delivered to the treatment site with the present invention does not vary with the length of the radiation source exposed. Limiting the total radiation dose independent of length may be clinically important to avoid adverse effects of overexposure to ionizing radiation.

Refer now to FIGS. 2A and 2B which illustrate detailed longitudinal cross-sectional views of the elongate wire 10 shown in FIGS. 1A and 1B, respectively. Elongate shaft 12 includes an outer tubular member 20 and a moveable core member 22 disposed therein. Moveable core member 22 may include a proximal stop 32 to limit longitudinal displacement of the core member 22 relative to the outer tubular member 20, thereby limiting longitudinal expansion of the tip 14. The elongate shaft 12 may have an outside diameter on the order of 0.010–0.040 inches and a length on the order of 150–350 cm to facilitate navigation through human vasculature, including the coronary vasculature. The elongate shaft 12 may be formed of virtually any suitable medical grade metal or polymer, but preferably the outer tubular member 20 is formed of a super-elastic alloy such as nickel titanium, and moveable core member 22 is formed of stainless steel. Those skilled in the art will recognize that the materials and dimensions of the elongate shaft 12 may be varied depending on the particular vascular anatomy being navigated.

As mentioned previously, the proximal end of the tip 14 is secured to the distal end 24 of the outer tubular member 20. Similarly, the distal end of the tip 14 is connected to the distal end 26 of the moveable core member 22. If a metal coil 28 is utilized for the tip 14 as illustrated, and if a metallic core member 22 is utilized, the distal end of the coil 28 may be welded to the distal end of the moveable core member 22 to form an a traumatic weld ball 26. Similarly, if a metallic outer tubular member 20 is utilized, the proximal end of the coil 28 may be connected to the distal end 24 of the outer tubular member 20 utilizing a solder joint 30. If dissimilar materials are used as between the tip 14 and the distal ends 24 and 26, a suitable medical grade adhesive may be used to make the connections.

Refer now to FIGS. 3, 4 and 5, which illustrate lateral cross-sectional views taken along lines 3—3, 4—4 and 5—5, respectively, in FIG. 2A. As can be seen in FIGS. 3 and 4, a gap 34 is provided between the moveable core member 22 and the outer tubular member 20 to minimize the friction therebetween. As can be seen in FIG. 5, a relatively small gap is formed between the moveable core member 22 and the distal end 24 of the outer tubular member 20. In particular, the distal end 24 of the outer tubular member 20 is tapered to reduce the outside and inside diameters. Reduction of the outside diameter facilitates connection to the proximal end of the tip 14 without increasing the profile at the juncture. Reduction of the inside diameter facilitates minimizing lateral displacement of the moveable core 22 as it moves therethrough.

In use, the elongate wire 10 embodiment may be used in conjunction with an afterloader and a centering device, both of which are well known in the art. If desired, the treatment site may be pre-dilated utilizing a balloon angioplasty catheter, an atherectomy catheter or other suitable PTCA device. Typically, a centering device, such as a balloon catheter with a segmented or helical balloon disposed at the distal end thereof, is navigated to the desired treatment site using a guide wire and conventional fluoroscopic techniques. Once the centering device is positioned adjacent the treatment site and inflated, the elongate radiation source wire 10 may be advanced through the centering device utilizing an afterloader. The afterloader may also be used to affect the change in length of the radiation source. Preferably prior to advancing the source wire 10, the length of the tip 14 may be adjusted to correspond to the length of the treatment site.

However, the length of the tip 14 may be varied during the procedure if desired. After sufficient dwell time (i.e., the time the tip 14 is positioned adjacent the treatment site), the elongate wire 10 may be withdrawn from the centering catheter utilizing the afterloader. Because the total radioactivity of the tip 14 remains constant and the radioactivity per unit length varies with changes in length, the dwell time may be adjusted to provide the desired dose to the particular treatment site. After or simultaneously with removal of the elongate wire 10, the centering device and all ancillary devices may then be removed, marking the completion of the procedure.

Figure 6A:
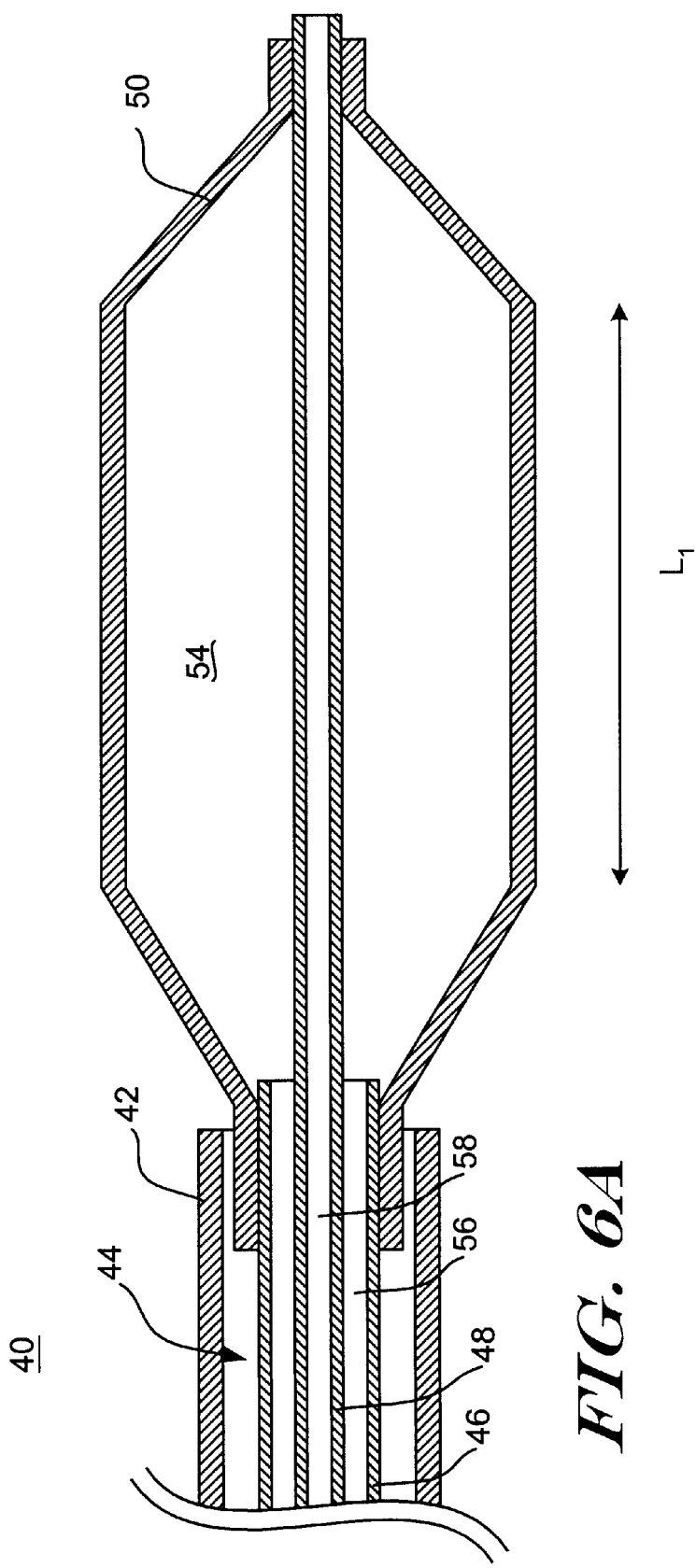
FIGS. 6A and 6B are longitudinal cross-sectional views of the present invention in the form of a balloon catheter having a variable-length balloon filled with radioactive fluid.
Figure 6B:
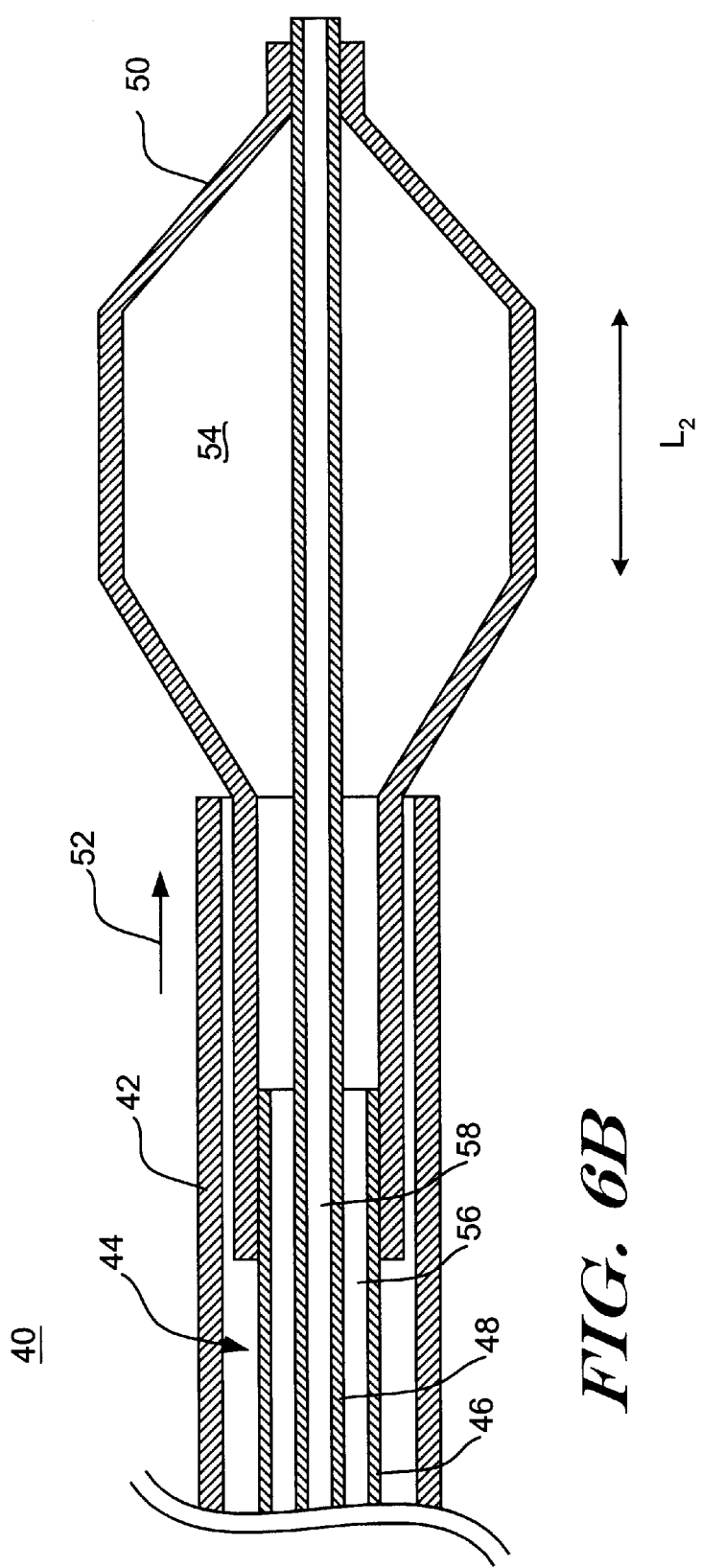

Refer now to FIGS. 6A and 6B which illustrate longitudinal cross-sectional views of the present invention in the form of a balloon catheter 40, having a variable length balloon 50 filled with a radioactive fluid. Balloon catheter 40 is similar to wire 10 in form and function except as described herein. Catheter 40 represents a generic catheter having a variable balloon for which there are a number of suitable specific embodiments. For example, suitable specific embodiments are disclosed in U.S. Pat. No. 4,564,014 to Fogarty et al., U.S. Pat. No. 5,246,421 to Saab, and co-pending patent application Ser. No. 08/950,520 now U.S. Pat. No. 5,961,536 to Mickley et al., each of which are fully incorporated herein by reference. For purposes of simplicity and clarity, only the distal portion of the catheter 40 has been illustrated in generic form.

Catheter 40 includes an outer sheath 42 slidably disposed about an inner catheter shaft 44. Inner catheter shaft 44 may include an outer tube 46 and an inner tube 48 co-axially disposed therein. An inflatable balloon is connected to the distal end of the inner catheter shaft 44. Specifically, the proximal end of the balloon 50 is connected to the distal end of the outer tube 46, and the distal end of the balloon 50 is connected to the distal end of the inner tube 48. Inner tube 48 defines a guide wire lumen 58 through which a conventional guide wire may be inserted. An inflation lumen 56 is defined by the annular space between the outer tubular member 46 and the inner tubular member 48. Inflation lumen 56 is in fluid communication with the interior 54 of the balloon 50 such that the balloon 50 may be inflated and deflated with a radioactive fluid. Such radioactive fluid may comprise a liquid having a radioactive isotope suspended therein. Other suitable radioactive fluids are known in the art.

As shown in FIG. 6A, outer sheath 42 may be retracted proximal of the balloon 50 expands unconstrained to its nominal length and diameter. Under this condition, the radioactive fluid disposed in the interior 54 of the balloon 50 provides a treatment length of approximately L1. As shown in FIG. 6b, outer sheath 42 may be longitudinally displaced in the distal direction as indicated by arrow 52 to radially constrain expansion of the balloon 50. With the outer sheath 42 so positioned, the balloon 50 defines a constrained portion and an expanded portion of the balloon 50 as an interior 54 filled with radioactive fluid to provide a treatment length of approximately L2. Accordingly, longitudinal displacement of the outer sheath 42 relative to the inner catheter shaft 44 and the balloon 50 causing the balloon 50 to change in length. Changes in length of the balloon 50 correspondingly changes the size of the expanded portion of the balloon and thus the size of the interior of the balloon containing radioactive fluid. In this manner, the outer sheath 42 may be longitudinally displaced to control the effective treatment length of the radioactive fluid contained in the interior 54 of the balloon 50.

Examples of catheters having inflatable balloons containing radioactive fluid may be found in U.S. Pat. No. 5,616, 114 to Thornton et al., International Patent Application Publication No. WO 97/40889 to Apple et al., and U.S. patent application Ser. No. 08/154,267 now U.S. Pat. No. 5,596,099 to Sahatjian, the entire disclosures of which are hereby incorporated by reference. In light of these disclosures, only the distal portion of the catheter 40 has been illustrated for purposes of clarity and simplicity.

Catheter 40 may be used substantially the same as described in U.S. Pat. No. 5,616,114 to Thornton et al., except that the length of the radiation source (i.e., balloon 50) may be adjusted by longitudinal displacement of the outer sheath 42 as described above.

Figure 7A:
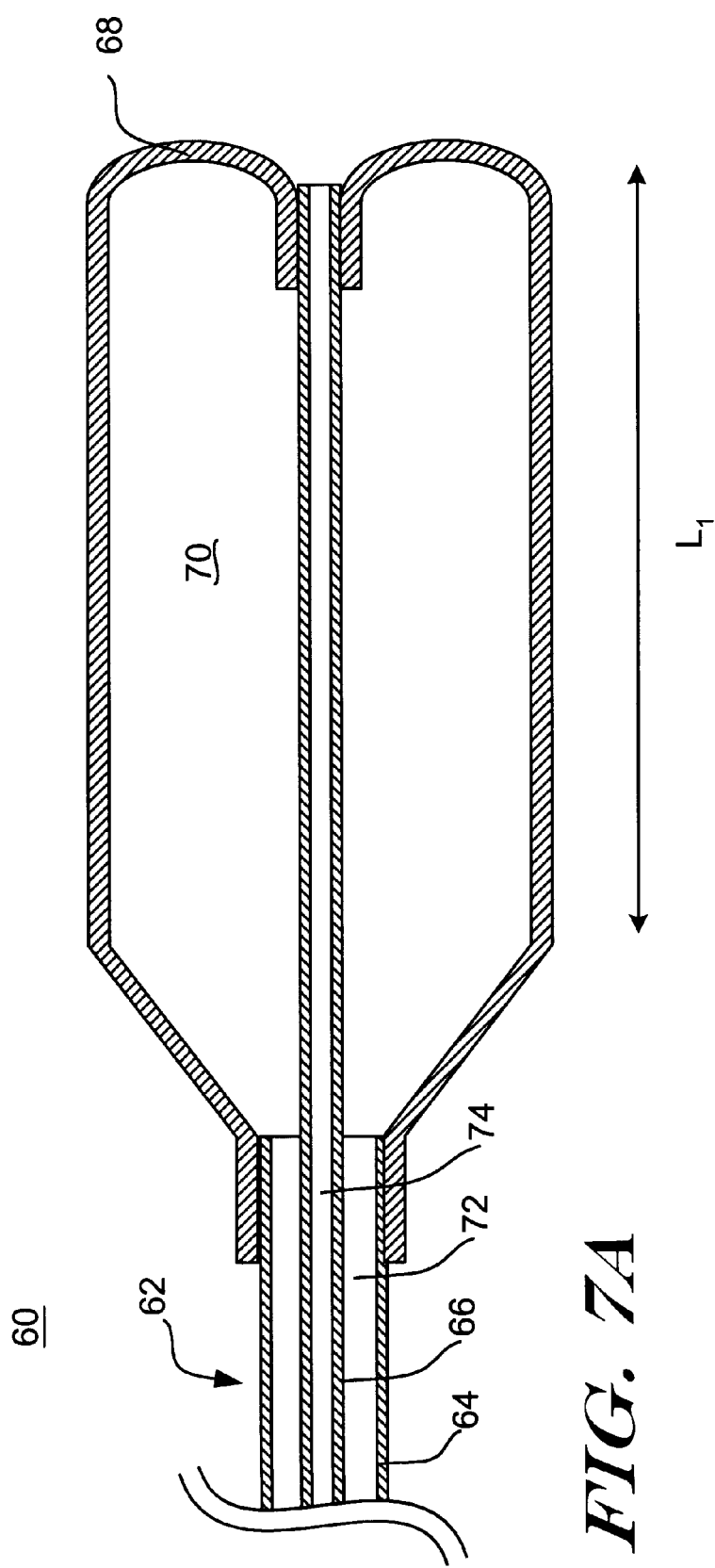
FIGS. 7A and 7B are longitudinal cross-sectional views of the present invention in the form of an alternative balloon catheter having a variable-length inverted balloon filled with radioactive fluid.
Figure 7B:
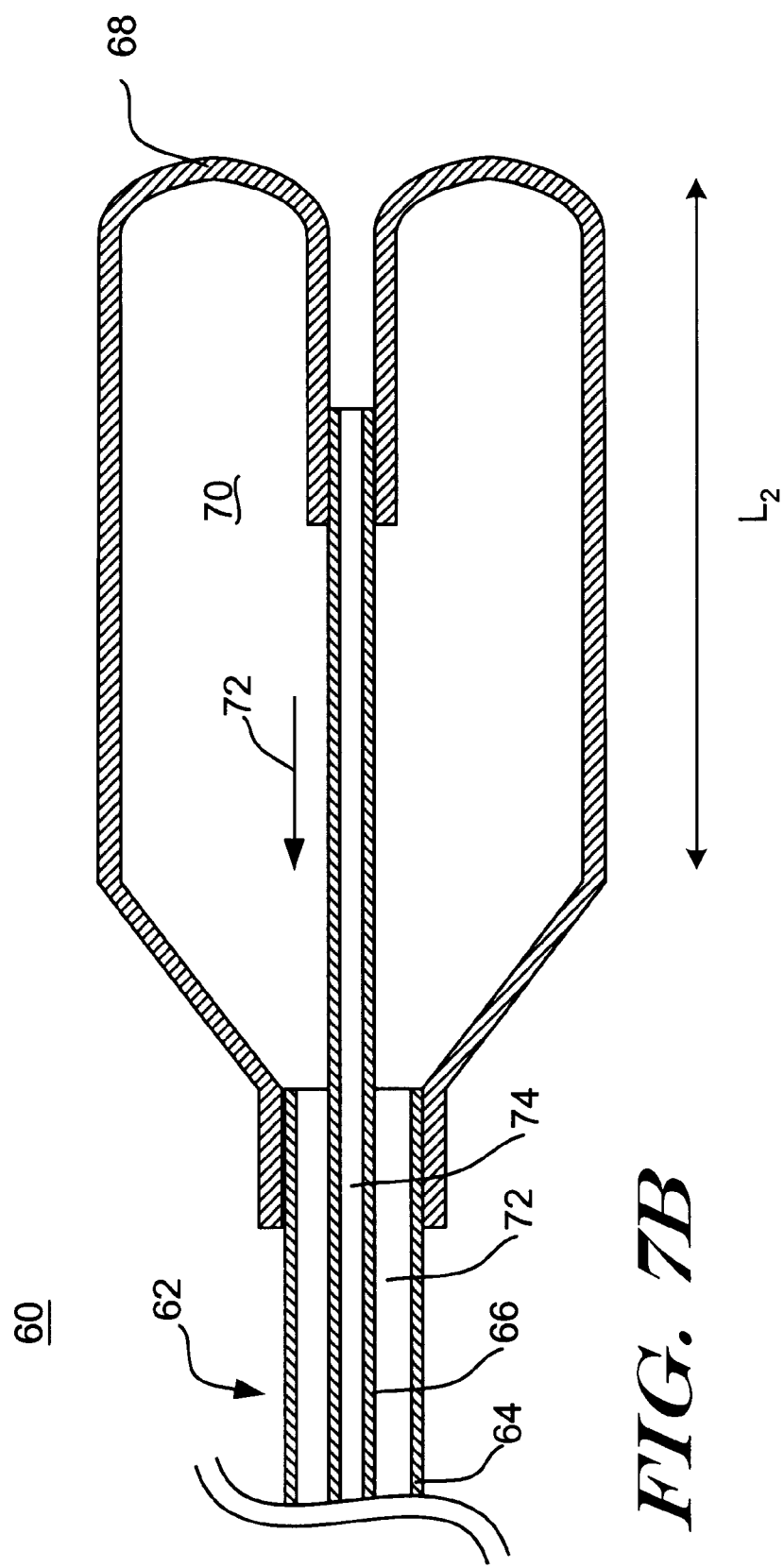

Refer now to FIGS. 7A and 7B which illustrate longitudinal cross-sectional views of the present invention in the form of an alternative balloon catheter 60 having a variable length inverted balloon 68. Catheter 60 is substantially the same as catheter 40 in both form and function, except as described herein. Catheter 60 represents a generic catheter having a variable length inverted balloon for which there are several corresponding specific embodiments. For example, U.S. Pat. No. 5,163,927 to Woker et al. and U.S. Pat. No. 5,171,305 to Schickling et al., both of which are hereby incorporated by reference, disclose specific embodiments of a catheter having an inverted balloon. In light of these disclosures, and the disclosure of U.S. Pat. No. 5,616,114 to Thornton et al., only the distal portion of the catheter 60 is illustrated for purposes of simplicity and clarity.

Catheter 60 includes an elongate shaft 62 having an outer tubular member 64 and inner tubular member 66 co-axially disposed therein. An inverting balloon 68 is connected to the distal end of the elongate shaft 62. Specifically, the proximal end of the inverting balloon 68 is connected to the distal end of the outer tubular member 64, and the distal end of the inverting balloon 68 is connected to the distal end of the inner tubular member 66. A guide wire lumen 74 is defined by the inner tubular member 66 and is adapted for insertion of a guide wire therein. An inflation lumen 72 is defined in the annular space between the outer tubular member 64 and the inner tubular member 66. Inflation lumen 72 is in fluid communication with the interior 70 of the balloon 68, which is filled with a radioactive fluid with inflated.

FIG. 7a illustrates the balloon 68 and the fully extended and inflated state wherein the interior 70 of the balloon contains a radioactive fluid to define a radioactive source having an approximate length of L1. As illustrated in FIG. 7b, the inner tubular member 66 may be retracted in a proximal direction as indicated by arrow 72 relative to the outer tubular member 64 to cause the balloon 68 to further invert thereby shortening the overall length of the balloon 68. By shortening the length of the balloon 68, the interior 70 of the balloon 68 correspondingly decreases in length such that the radioactive fluid disposed in the interior 70 of the balloon 68 as a reduced length L2. With this arrangement, longitudinal displacement of the inner member 66 relative to the outer member 64 may be used to control the length of the radiation source (i.e., the radioactive fluid disposed in the interior 70 of the balloon 68. Inner tubular member 66 is longitudinally movable relative to the outer tubular member 64.

Catheter 60 may be used substantially the same as catheter 40, except that longitudinal displacement of the inner tubular member 66 causes variation of length of the radiation source.

Figure 8A:
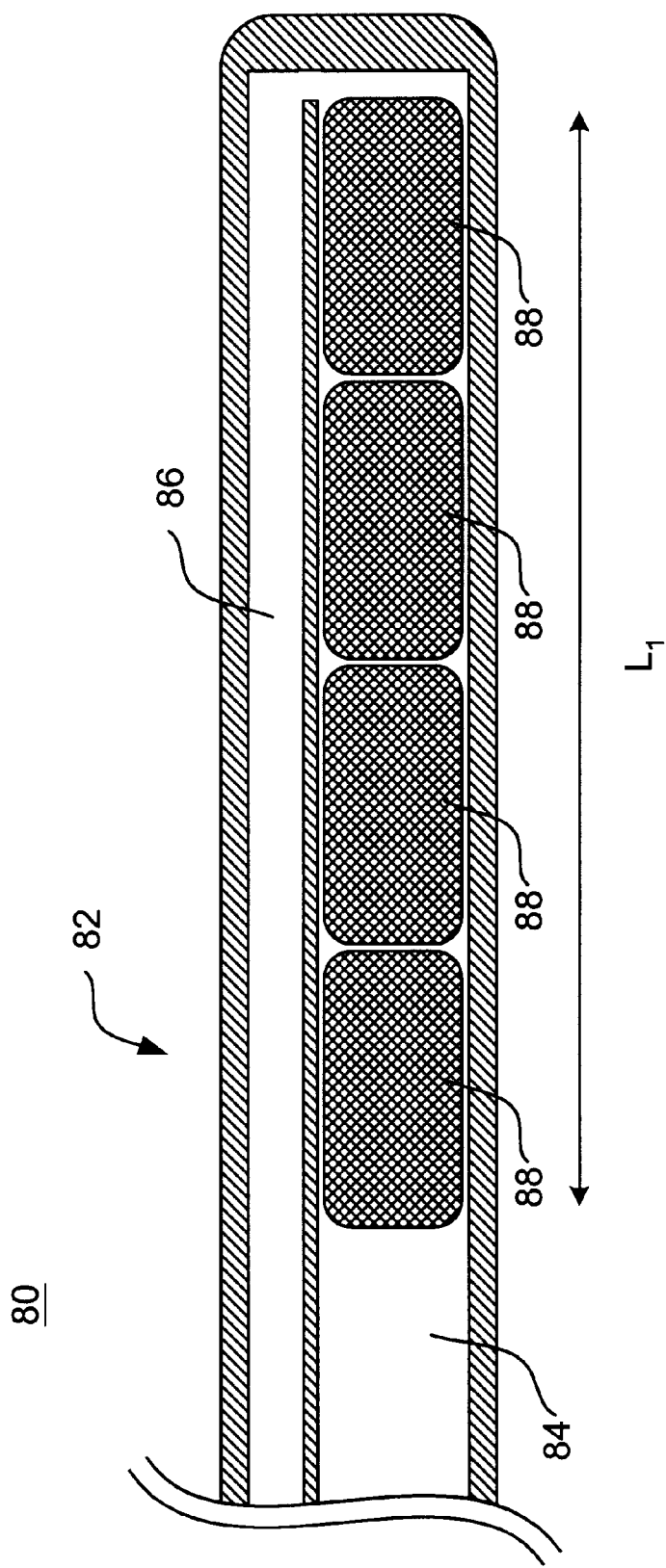

Refer now to FIGS. 8A and 8B which illustrate longitudinal cross-sectional views of the present invention in the form of a catheter 80 having means for advancing and retracting radioactive seeds 88 of variable number. Except as described herein, catheter 80 is similar to other embodiments of the present invention previously described. Catheter 80 represents a generic catheter for advancing and retracting radioactive seeds. Specific embodiments of such a catheter may be found in U.S. Pat. No. 5,683,345 to Waksman et al. and U.S. patent application Ser. No. 08/866,560 now U.S. Pat. No. 6,019,718 to Hektner et al., the disclosures of which are hereby incorporated by reference. Waksman et al. disclose a device wherein the radioactive seeds are advanced and retracted pneumatically. Hektner et al. disclose a catheter wherein the radioactive seeds are advanced and retracted mechanically as with a string or cable. Although illustrated as utilizing pneumatic means, catheter 80 is illustrated in generic form and may readily utilize either pneumatic or mechanical means to advance and retract the radioactive seeds. In addition, in light of these disclosures, only the distal portion of the catheter 80 has been illustrated for purposes of clarity and simplicity.

Catheter 80 includes an elongate shaft having a delivery lumen 84 and a return lumen 86. Delivery lumen 84 is sized to accommodate radioactive seeds 88 such that the seeds may be readily transported pneumatically from the proximal end of the shaft 82 to the distal end of the shaft 82. Return lumen 86 is sized to provide a fluid path such that the distal end of the delivery lumen 84 may be pressurized causing the radioactive seeds 88 to return to the proximal end of the elongate shaft 82. The proximal end of the elongate shaft 82 may be connected to an after-loader (not shown) which incorporates a means to vary the number of radioactive seeds 88 delivered to the distal end of the catheter 80.

Such means may comprise, for example, a cartridge containing the maximum number of seeds 88 usable with the catheter 80 from which the physician may select the desired number seeds 88. The desired number of seeds 88 may be automatically or manually loaded into the delivery lumen 84. For example, to select the desired number, a pin may be placed in a slot in the cartridge behind a row seeds 88 totaling the desired number. The pin may then be advanced in the slot thereby pushing the desired number of seeds 88 into the proximal end of the delivery lumen 84. Alternatively, by using a spring loaded cartridge, seeds 88 may be individually advanced into the proximal end of the delivery lumen until reaching the desired number. Those skilled in the art will recognize that many different cartridge designs may be employed in addition to other similarly functioning designs to vary the number of radioactive seeds 88. Adaptable designs are disclosed in U.S. Pat. No. 5,860,909 to Mick and U.S. Pat. No. 5,342,283 to Good, both of which are hereby incorporated by reference.

By changing the number of radioactive seeds 88 delivered to the distal end of the catheter 80, the effective length of the radioactive source may be changed. As illustrated in FIG. 8A, catheter 80 has several radioactive seeds 88 disposed in the distal end of the shaft 82 to define a relatively long radioactive section having a length L1. As shown in FIG. 8B, fewer radioactive seeds 88 are disposed in the distal end of the elongate shaft 82 to define a relatively short radioactive section having a length L2 wherein L2 is less than L1. Accordingly, by utilizing the means for varying the number of radioactive seeds to be delivered through the delivery lumen 84, the overall length of the radiation source may be varied.

Figure 9A:
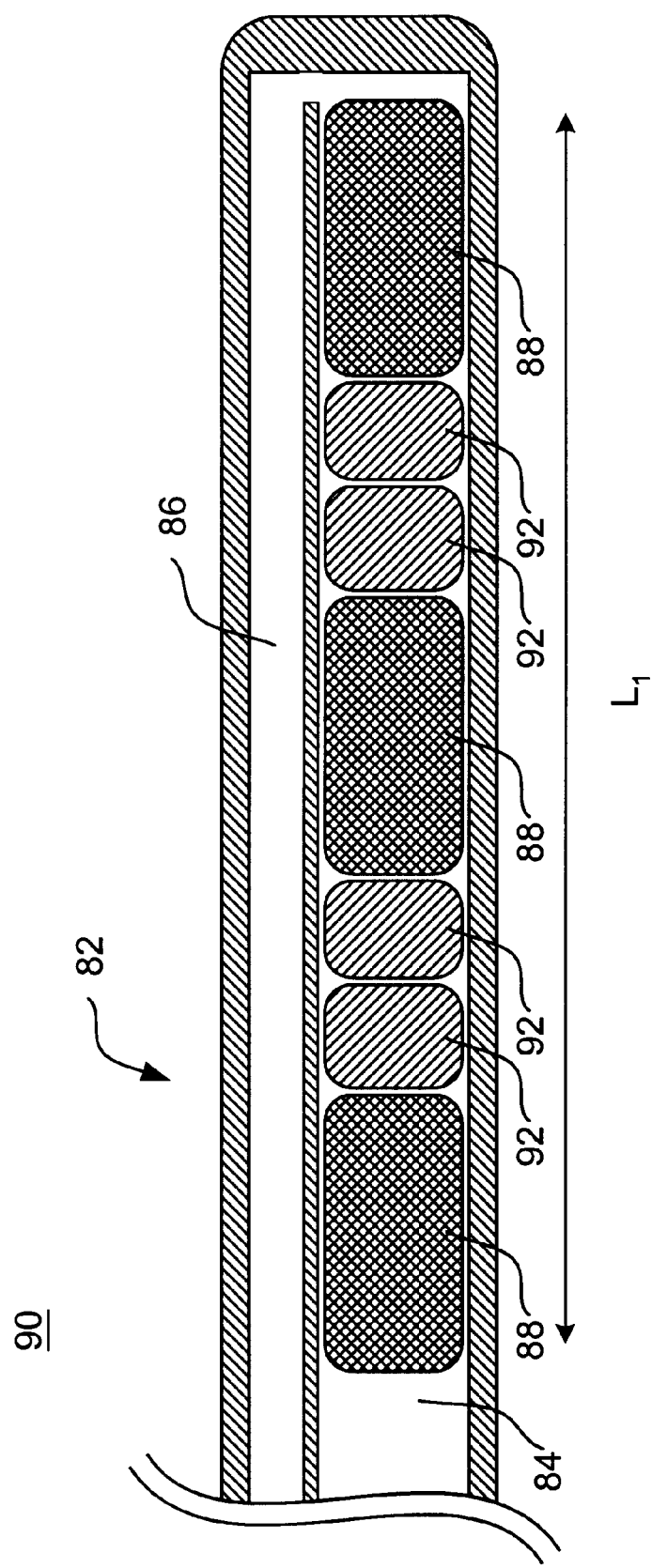
FIGS. 9A and 9B are longitudinal cross-sectional views of the present invention in the form of a catheter having means for advancing and retracting radioactive seeds of variable spacing.
Figure 9B:
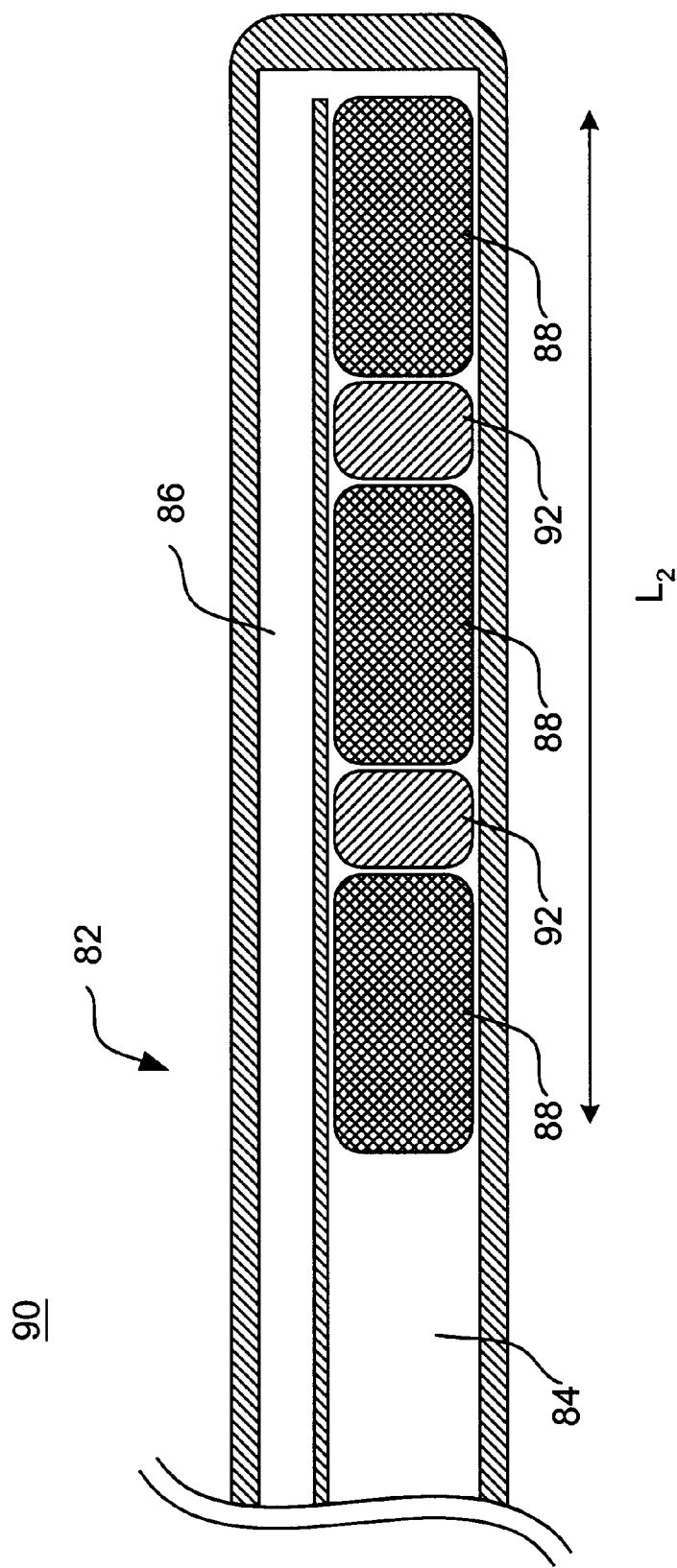

Refer now to FIGS. 9A and 9B which illustrate longitudinal cross-sectional views of the present invention in the form of a catheter 90 having means for advancing and retracting radioactive seeds of variable spacing. Except as described herein, catheter 90 is substantially the same in form and function as catheter 80.

Catheter 90 includes an elongate shaft 82 having a delivery lumen 84 and a return lumen 86. The plurality of radioactive seeds are disposed in the distal end of the delivery lumen 84. Non-radioactive spacers 92 are disposed between each of the radioactive seeds 88. Non-radioactive spacers 92 may comprise any inert material.

The proximal end of the catheter 90 may be connected to an after loader containing a means for varying the number of spacers 92 disposed between the radioactive seeds 88. The means for varying the number of spacers 92 may be substantially the same as the means for varying the number of radioactive seeds as described with reference to catheter 80.

As illustrated in FIG. 9A, catheter 90 includes several spacers 92 disposed between the radioactive seeds 88 to define a radiation source having a relatively long length L1. FIG. 9B illustrates fewer spacers 92 disposed between adjacent radioactive seeds 88 to define a radiation source having a relatively short length L2, wherein L2 is less than L1. With this arrangement, the overall length of the radiation source as defined by the length of the radioactive seeds 88 and spacers 92 may be varied by varying the number of spacers disposed between adjacent seeds 88.

Catheters 80 and 90 may be used substantially the same as described by Waksman et al. except that the number of radioactive seeds 88 and/or the number of spacers disposed between adjacent radioactive seeds may be varied to vary the length of the radioactive source.

From the foregoing, it should be apparent that the present invention provides a variable-length radiation source to compensate for any mismatch in length that would otherwise occur between a fixed-length radiation source and the treatment site. Thus, the variable-length radiation source of the present invention provides a means to match the radiation source length to the length of the treatment site, thus mitigating against overexposure and underexposure. In addition, the variable-length design of the present invention reduces the inventory that must be kept on hand to treat different patients with different treatment site lengths, thereby reducing the otherwise significant cost of storing radioactive material.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A medical device for intravascular ionizing radiation therapy, comprising:

an elongate shaft having a proximal end and a distal end, the elongate shaft including an inner member and an outer member wherein the inner member is longitudinally movable relative to the outer member; and a variable-length ionizing radiation source disposed on the distal end of the shaft, wherein a proximal end of the radiation source is connected to a distal end of the outer member, and a distal end of the radiation source is connected to a distal end of the inner member.

2. A medical device as in claim 1, wherein the radiation source comprises an extendable tip including a radioactive material.

3. A medical device as in claim 2, wherein the extendable tip is a coil.

4. A medical device as in claim 1, wherein longitudinal displacement of the inner member relative to the outer member causes corresponding longitudinal displacement of the distal end of the radiation source.

5. A medical device as in claim 4, wherein the longitudinal displacement of the distal end of the radiation source causes length variation of the radiation source.

6. A medical device as in claim 5, wherein the inner member includes a stop disposed on a proximal end thereof to limit length variation of the radiation source.

7. A medical device as in claim 5, wherein the radiation source comprises a extendable tip.

8. A medical device as in claim 5, wherein the radiation source comprises an inverting balloon.

9. A medical device for intravascular ionizing radiation therapy, comprising:

an elongate shaft having a proximal end and a distal end;

an ionizing radiation source comprising a variable-length tip disposed on the distal end of the shaft; and means for varying the length of the radiation source, wherein the means for varying the length of the radiation source comprises a movable member connected to an end of the variable-length tip.

10. A method of delivering ionizing radiation to a treatment site inside a patient's vasculature, comprising the steps of:

providing a medical device including an elongate shaft having a variable-length ionizing radiation source comprising a variable-length lip disposed on a distal end of the shaft and a means for varying the length of the radiation source, wherein the means for varying the length of the radiation source comprises a movable member connected to an end of the vanable-length tip;

inserting the medical device into the vasculature of the patient;

changing the length of the radiation source; and removing the medical device from the vasculature of the patient.

11. A method as in claim 10, wherein the step of changing the radioactive length is performed prior to the step of inserting the medical device into the vasculature of the patient.

12. A method as in claim 10, wherein the step of changing the radioactive length is performed after to the step of inserting the medical device into the vasculature of the patient.

* * * * *

UNITED STATES PATENT AND TRADEMARK OFFICE
CERTIFICATE OF CORRECTION

PATENT NO. : 6,352,501
DATED : March 05, 2002
INVENTOR(S) : Michael J. Urick

Page 1 of 1

It is certified that error appears in the above-identified patent and that said Letters Patent is hereby corrected as shown below:

<u>Column 12,</u>
Line 4, delete "lip" and insert -- tip --.
Line 8, delete "vanable" and insert -- variable --.

Signed and Sealed this

Twenty-first Day of May, 2002

Attest:

Attesting Officer

JAMES E. ROGAN
Director of the United States Patent and Trademark Office